United States Patent [19]

Ohsaki

[11] Patent Number: 4,573,990
[45] Date of Patent: Mar. 4, 1986

[54] DISPOSABLE DIAPERS

[75] Inventor: Hiroaki Ohsaki, Nagoya, Japan

[73] Assignee: Ohsaki Eisei Zairyo K.K., Nagoya, Japan

[21] Appl. No.: 673,350

[22] Filed: Nov. 20, 1984

[30] Foreign Application Priority Data

Nov. 24, 1983 [JP] Japan .................. 58-222895

[51] Int. Cl.⁴ .............................. A61F 13/16
[52] U.S. Cl. .............................. 604/385 R
[58] Field of Search .................. 604/385, 372

[56] References Cited

U.S. PATENT DOCUMENTS

| | | | |
|---|---|---|---|
| 3,943,930 | 3/1976 | Schaar | 604/385 |
| 4,251,643 | 2/1981 | Harada et al. | 604/372 |
| 4,360,022 | 11/1982 | Usami et al. | 604/385 |

*Primary Examiner*—C. Fred Rosenbaum
*Assistant Examiner*—Sherri Vinyard
*Attorney, Agent, or Firm*—Dennison, Meserole, Pollack & Scheiner

[57] ABSTRACT

Disclosed herein is a disposable diaper formed from a web of layered material consisting of a water-absorbent, non-woven top sheet, a waterproof backing sheet bonded on its peripheral margins to the top sheet to thereby form a generally rectangular bag, and at least one layered middle pad encased in the bag. The web, with the top sheet facing up, is folded along its longitudinal center line into a generally inverted Ω-shaped vertical cross-sectional configuration and subsequently folded intermediate the opposite transverse ends thereof into a generally S-shaped vertical cross-sectional configuration whereby the front half of the web can be served as a front diapering area and the rear half of the web can be served as a rear diapering area. The S-shaped folded area of the web is bonded on the opposite longitudinal lapping margins to thereby form a pocket contiguous to the front diapering area of the web.

2 Claims, 12 Drawing Figures

DISPOSABLE DIAPERS

BACKGROUND OF THE INVENTION

This invention relates to a disposable diaper used for both adults and infants.

Disposable diapers have heretofore been available for invalids and infants who cannot go to a toilet by themselves. Although the previously known diapers have generally been successful in receiving urine and feces, they have often created one or more collateral problems. The conventional diaper sometimes fails to satisfactorily receive human waste, thereby causing the waste to leak out of the diaper. The leaked waste will then soil clothing and bedding or in other instances, contaminate the body of an invalid or an infant, causing undesired infection such as dermatitis, rash and decubitus.

SUMMARY OF THE INVENTION

It is, accordingly, the primary object of the present invention to avoid the noted disadvantages of the prior art diaper by providing a pair of individual reception spaces in a diaper for receiving urine and feces, respectively, and to thereby provide an improved diaper which may prevent leaking and/or oozing of urine and feces, which may eliminate the possibility of soiling clothing and/or bedding and which may render no discomfort to the user of such diaper.

The diaper of the invention has two distinct areas: a front diapering area which is applicable to the abdominal region of a human body and a rear diapering area which is applicable to the buttocks of a human body. The diaper is formed from a web of layered material which consists of a water-absorbent, non-woven top sheet to be worn next to the skin of a human body; a waterproof backing sheet bonded on its peripheral margins to the top sheet to thereby form a bag; and a pair of water-absorbent, layered middle pads Q encased in the bag. The basic web, with the top sheet facing up, is folded at its opposite longitudinal sides into a generally inverted Ω-shaped vertical cross-sectional configuration. The web is further folded forwardly at the medial portion thereof into a generally S-shaped vertical cross-sectional configuration. The opposite longitudinal lapping margins of the folded area are bonded as by sealing to form a pocket contiguous to the front diapering area. The pocket is adapted to receive urine therein, and the rear diapering area is adapted to receive feces centrally in the inverted Ω-shaped recess. Thus, the specific arrangement enables urine and feces to be separately received within the diaper, thereby positively preventing urine and feces from being mingled. The diaper of the invention may also prevent leaking of human wastes, thereby reducing discomfort of the user.

The present invention will become more fully apparent from the claims and description as it procedes with the drawings.

DETAILED DESCRIPTION OF THE PREFERRED EMBODIMENT

The drawings illustrate a disposable diaper of the invention in various phases of its formation. For convenience in describing the relative position of the several parts, the left end of the diaper illustrated in FIGS. 1 through 10 is referred to as the front of the diaper; and forward and rearward parts and movements will be in relation to this front of the diaper.

Figure 1:
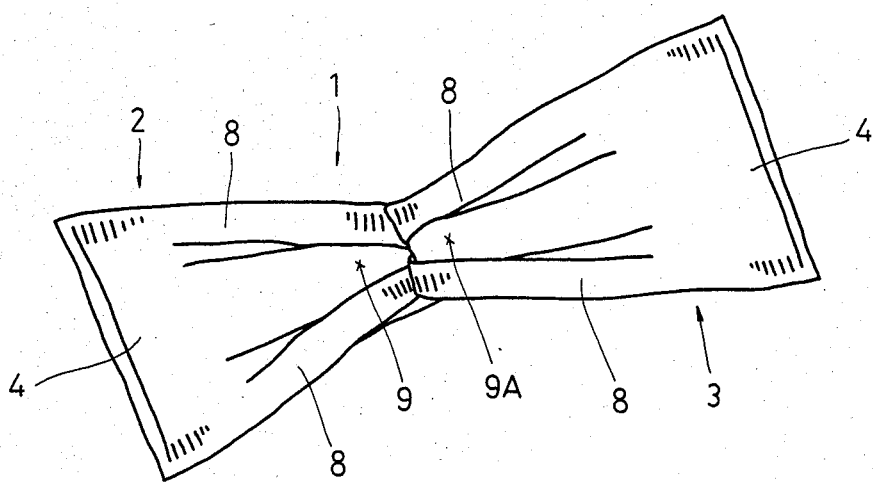
FIG. 1 is a perspective view of a disposable diaper of the invention.

Referring to the drawings and to FIG. 1 in particular, shown therein and generally designated by the reference numeral 1 is a disposable diaper formed in accordance with the invention. As shown therein, the diaper 1 is comprised of a front diapering area 2 adapted to cover the abdominal region of a human body and a rear diapering area 3 adapted to cover the buttocks, so that the diaper 1 may be applied to the human body between the abdominal region and the buttocks.

Figure 6:
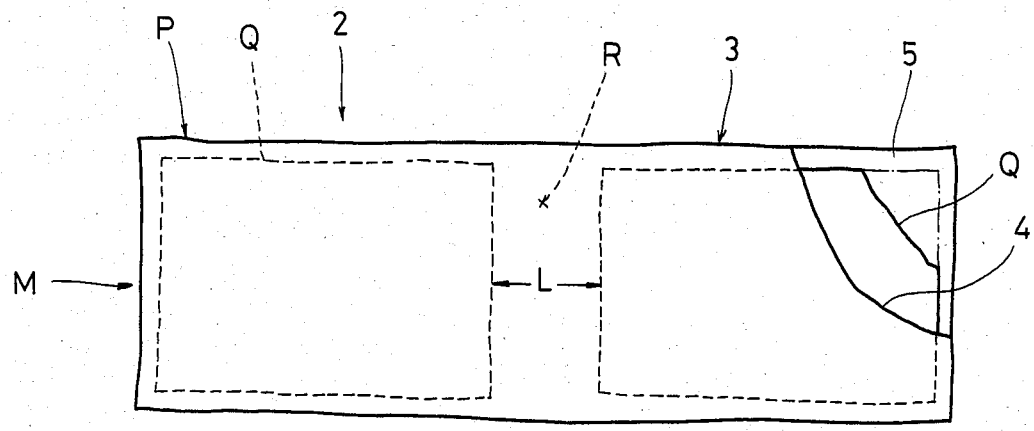
FIG. 6 is a plan view of a web of layered material from which the diaper is formed.
Figure 12:
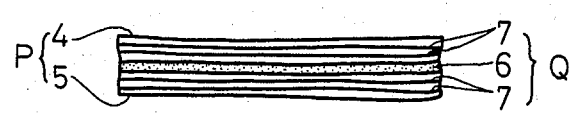
FIG. 12 is an enlarged sectional view of a portion of a layered middle pad.

Referring now to FIG. 6, shown therein and generally designated by the alphabet M is a web of layered material from which the diaper 1 of the invention is formed. The web M is formed with a water-absorbent, non-woven top sheet 4 and a waterproof backing sheet 5 of polyethelene, the top sheet 4 and the backing sheet 5 being superposed and sealed on their peripheral margins, and formed into bag P. In the embodiment illustrated, a pair of layered middle pads Q are encased in the front and rear halves of the bag P in such a manner as to provide a blank area R having a predetermined width L in the medial portion of the web M between the pads Q. Specifically, as shown in FIG. 12, each of the pads Q is formed with a high-molecular, water-absorbent solidification sheet 6 interposed between an upper and lower layers of water-absorbent paper cotton 7. The water-absorbent solidification sheet 6 is formed from a crushed pulp (or a paper cotton) and a granulated high-molecular absorbent which are superposed and compressed into a sheet. Thus, upon absorption of moisture of human waste, the subjected area will be solidified in a short period of time, thereby preventing possible ooze and viscosity of human waste.

Figure 7:
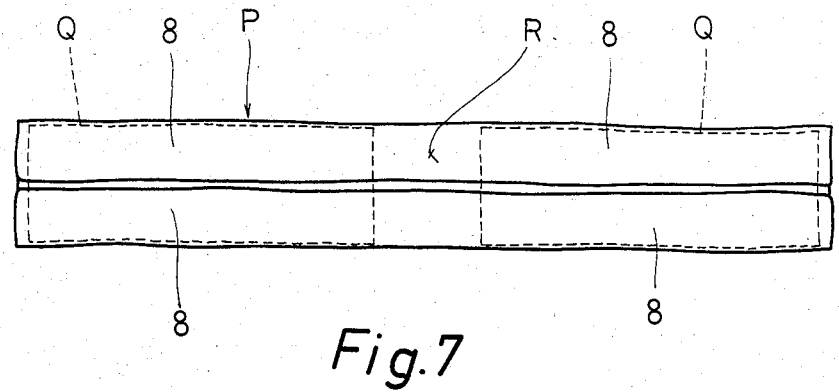
FIG. 7 is a plan view showing the web in the folded state to a generally inverted Ω-shaped configuration.
Figure 11:
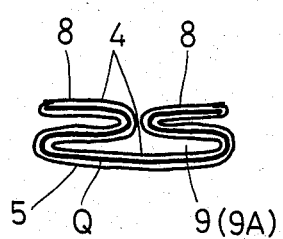
FIG. 11 is a sectional view taken substantially along the lines XI—XI of FIG.10.

To form a diaper 1 of the invention, as shown in FIGS. 7 and 11, the web M, with the top sheet 4 facing up, is folded at its opposite longitudinal sides into a generally inverted Ω-shaped vertical cross-sectional configuration including a pair of upturned areas 8, thereby providing a first reception space 9 centrally in the front diapering area 2 and a second reception space 9A also centrally on the rear diapering area 3.

Figure 8:
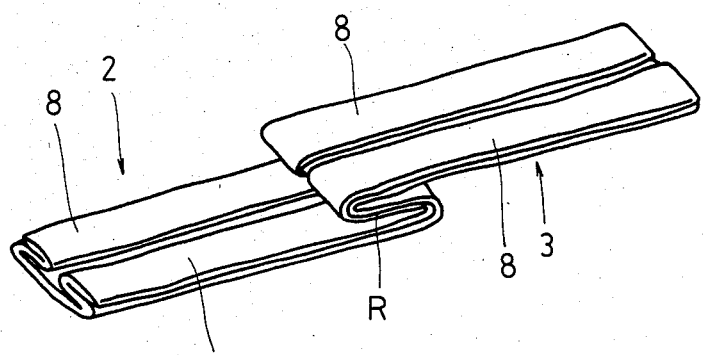
FIG. 8 is a perspective view of the web folded as shown in FIG. 7, with the medial portion thereof shown in the folded state to a S-shaped configuration.
Figure 9:
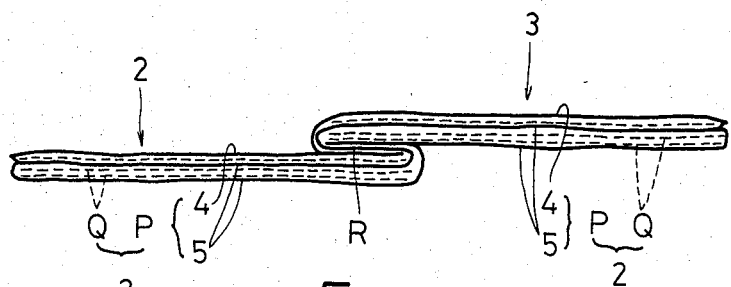
FIG. 9 is a side view of the web shown in FIG. 8.
Figure 10:
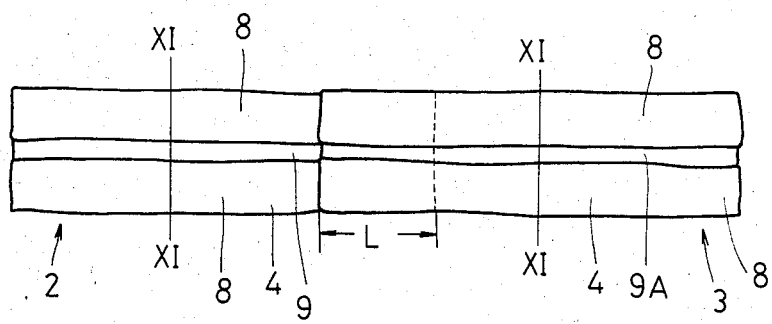
FIG. 10 is a plan view of the web shown in FIG. 8.

Thereafter, the web M is folded forwardly at the blank area R over the rear part of the front diapering area 2, and then the rear diapering area 3 is folded rearwardly, as shown in FIGS. 8 through 10. Specifically, the web M is so folded as to form a generally S-shaped vertical cross-sectional configuration with the blank area R interposed between the front and rear diapering areas 2 and 3. Further, the opposite londitudinal lapping margins of the folded blank area 8 are bonded as by sealing to form a final product, the diaper 1.

The diaper 1 thus constructed provides a pocket 10 for receiving urine which is defined between the upturned blank area R and the top sheet 4 of the front diapering area 2; and a concave recess of the second reception space 9A for receiving feces which is formed generally between the upturned areas 8 on the opposite longitudinal sides of the rear diapering area 3, thereby preventing feces from mingling with urine in the pocket 10. It will be noted that the diaper 1 described herein is particularly applicable to men, and when the diaper 1 is applied to women, it has to include a sanitary napkin (not shown) in the pocket 10 in view of the difference in genitalia structure. Thus, the provision of napkin will facilitate the introduction of urine into the first reception space 9 and the pocket 10.

Figure 2:
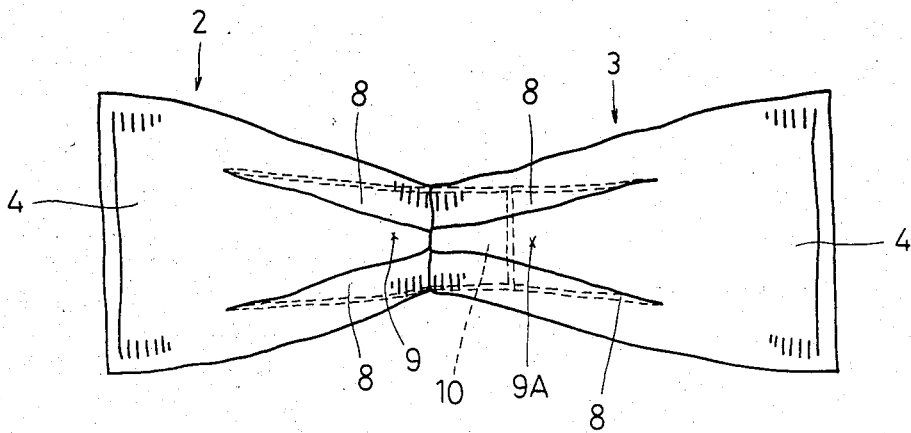
FIG. 2 is a plan view of the diaper shown in FIG. 1.
Figure 3:
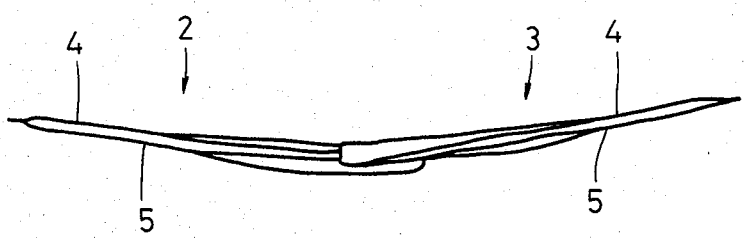
FIG. 3 is a side view of the diaper shown in FIG. 1.
Figure 4:
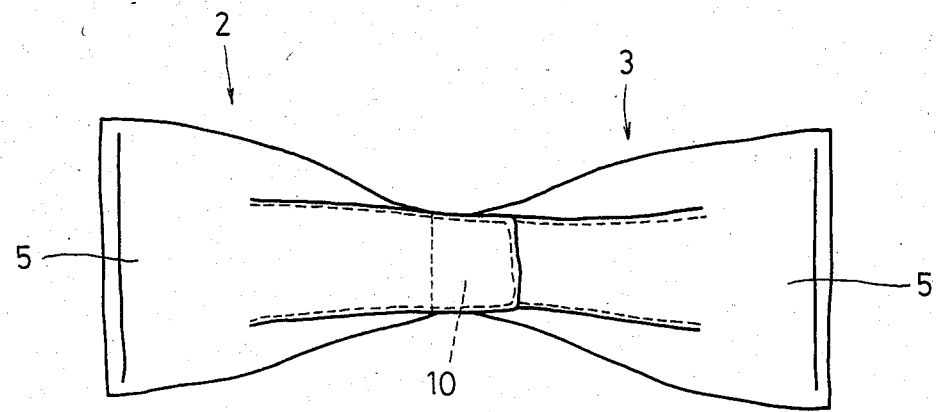
FIG. 4 is a bottom view of the diaper shown in FIG. 1.
Figure 5:
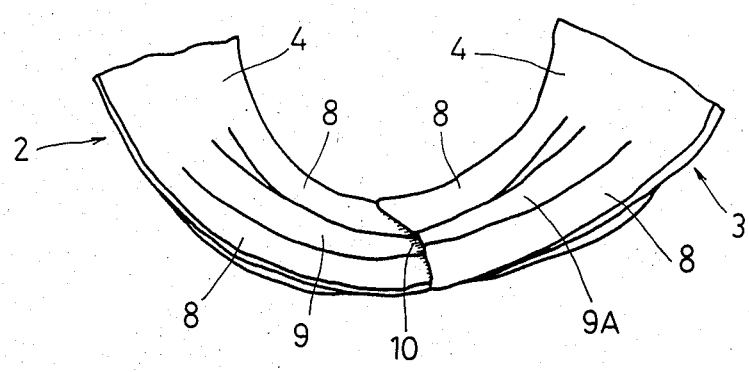
FIG. 5 is a perspective view, partially cut away, of a diaper of the invention, with the diaper shown in the inwardly bent state as is fitted over a human body.

To use the diaper 1, the front and rear diapering areas 2 and 3 are spread out toward the opposite transverse ends, respectively, like an unfolded fan as shown in FIGS. 1, 2 and 4. Then, the front diapering area 2, with the top sheet 4 facing inside is applied to the abdominal region of a human body, the medial portion of reduced width to the groin, and the rear portion of the rear diapering area 3 to the buttocks. The diaper 1 is then closely fastened to the body as by a diaper cover. In use, since the top cloth 4 of unwoven soft material is worn next to the skin, the diaper 1 will offer no discomfort to the user.

Further, it will be noted that the urinary organs of a human body are located generally at the first reception space 9 above the pocket 10 of the front diapering area 2; and the anal region is located generally at the second reception space 9A of the rear diapering area 3. Thus, in the event that a patient with the diaper 1 passes urine while lying on his side, the urine flows into the pocket 10 via the first reception space 9 of the front diapering area 2. As should be apparent, the pocket 10 is operable to prevent the urine from flowing outside. In the event that fecal material is discharged from the anus, the usually solidified fecal material will be received in the second reception space 9A of the rear diapering area 3. Again, the fecal material, being blocked by the upturned areas 8, will hardly flow out of the diaper 1.

The urine, discharged in the first reception space 9 and the pocket 10, is permeated into the top sheet 4, subsequently into the paper cotton 7 of the pad Q, and ultimately into the solidification sheet 6. The urine permeated in the solidification sheet 6 is solidified in a short period of time, and will hardly permeate downwardly. If urine permeates, however, the backing sheet 5 will block the ooze, thereby eliminating the possibility of soiling clothing and bedding. Similarly, feces in the second reception space 9A of the rear diapering area 3 will not ooze out, and moisture contained in feces are permeated and solidified in the solidification sheet 6.

In the embodiment illustrated, the separate middle pads Q are encased in the front and rear diapering areas 2 and 3, respectively, with the blank area R interposed therebetween. This particular arrangement will advantageously preclude the possibility of communication of moisture by capillarity between the respective pads Q encased in the bag P. However, it is to be understood that the invention is not limited to the specific arrangement of pads Q. Such pads Q may be integrally formed into a single piece which is extended substantially over the entire area within the bag P.

While a preferred embodiment of the invention has been described using specific terms, such description is for illustrative purposes only, and it is to be understood that changes and variations may be made without departing from the spirit or scope of the following claims.

What is claimed is:

1. A disposable diaper comprising a web of layered material including a water absorbent, non-woven top sheet, a waterproof backing sheet bonded to said top sheet at their peripheral margins to form a generally rectangular bag having longitudinal and transverse edges, and at least one layered middle pad encased in said bag, and extending over substantially the entire area of said bag;

said web having a front portion serving as a front diapering area applicable to the abdomen of a human body, a rear portion serving as a diapering area applicable to the buttocks of a human body, and a medial portion therebetween;

said web, with said top sheet facing up, being folded along its longitudinal center line into a generally inverted Ω-shaped vertical cross sectional configuration, and subsequently being folded intermediate the transverse edges of said bag and along the transverse edges of said medial portion into a generally S-shaped vertical cross-sectional configuration, wherein the contiguous, longitudinal edges of said bag in the S-shaped folded area are bonded together to form a pocket open at the transverse edge contiguous to said front diapering area, said pocket being located to receive urine and retain urine separate from feces, which is received in said rear diapering area.

2. A disposable diaper as defined in claim 1, wherein said at least one layered middle pad comprises a first middle pad encased in said front portion, and a second middle pad encased in said rear portion, said first and second middle pads each spaced a predetermined distance intermediate the opposite transverse ends of said web.

* * * * *